United States Patent [19]

Hromatka et al.

[11] 4,224,445
[45] Sep. 23, 1980

[54] THIENOTHIAZINE DERIVATIVES

[75] Inventors: Otto Hromatka; Dieter Binder, both of Vienna, Austria; Rudolf Pfister, Basel; Paul Zeller, Allschwil, both of Switzerland

[73] Assignee: Hoffmann-La Roche Inc., Nutley, N.J.

[21] Appl. No.: 955,568

[22] Filed: Oct. 30, 1978

Related U.S. Application Data

[62] Division of Ser. No. 852,385, Nov. 17, 1978, Pat. No. 4,134,898, which is a division of Ser. No. 606,563, Aug. 21, 1975, Pat. No. 4,076,709.

[30] Foreign Application Priority Data

Aug. 26, 1974 [CH] Switzerland ..................... 11582/74
Sep. 9, 1974 [CH] Switzerland ..................... 12157/74
Jul. 9, 1975 [CH] Switzerland ..................... 8963/75

[51] Int. Cl.³ ................. C07D 333/38; C07D 333/40
[52] U.S. Cl. ..................................... 544/212; 544/327; 544/331; 544/405; 546/284; 548/128; 548/195; 548/245; 548/246; 549/64
[58] Field of Search ............... 260/332.2 R; 544/64, 544/212, 327, 331, 405; 546/284; 548/128, 195, 245, 246

[56] References Cited

U.S. PATENT DOCUMENTS 4,076,709  2/1978  Hromatka .................... 260/332.2

Primary Examiner—Robert Gerstl
Attorney, Agent, or Firm—Jon S. Saxe; Bernard S. Leon; Frank P. Hoffman

[57] ABSTRACT

The present invention relates to compounds of the formula

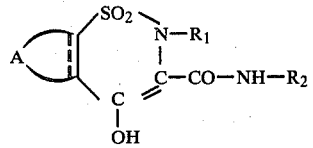

wherein A together with the two carbon atoms to which it is attached forms the group

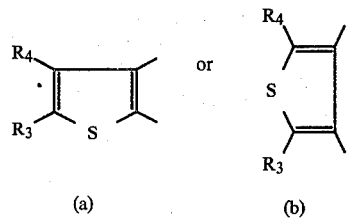

and the broken line represents the double bond in group (a); $R_1$ represents a lower alkyl group; $R_2$ represents the residue of an aromatic heterocyclic ring containing from 1 to 4 hetero atoms, which may be substituted by one or two lower alkyl groups, or a phenyl group which may be substituted by halogen, hydroxy, lower alkyl, trifluoromethyl or lower alkoxy and $R_3$ and $R_4$ each represent a hydrogen atom or a lower alkyl group.

Also provided are methods for their preparation. The thienothiazine derivatives provided by this invention have anti-flammatory, analgesic and anti-rheumatic activity.

1 Claim, No Drawings

THIENOTHIAZINE DERIVATIVES

This is a division, of application Ser. No. 852,385 filed Nov. 17, 1978, now U.S. Pat. No. 4,134,898 which is a divisional of 606,563, filed Aug. 21, 1975, now U.S. Pat. No. 4,076,709, issued Feb. 28, 1978.

DESCRIPTION OF THE INVENTION

The present invention relates to thiazine derivatives. More particularly, the invention is concerned with thienothiazine derivatives, a process for the manufacture thereof and pharmaceutical preparations containing same.

The thienothiazine derivatives provided by the present invention have the following general formula

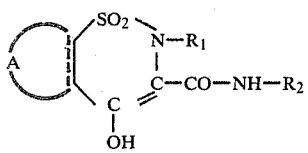   I wherein A together with the two carbon atoms to which it is attached forms the group

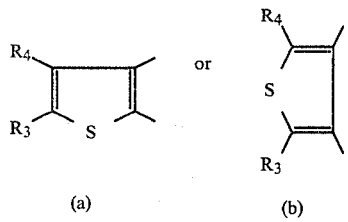

and the broken line represents the double bond present in group (a); $R_1$ represents a lower alkyl group; $R_2$ represents the residue of an aromatic heterocyclic ring containing from 1 to 4 hetero atoms, which may be substituted by one or two lower alkyl groups, or a phenyl group which may be substituted by halogen, hydroxy, lower alkyl, trifluoromethyl or lower alkoxy and $R_3$ and $R_4$ each represent a hydrogen atom or a lower alkyl group.

As used in this description and in the accompanying claims, the term "lower alkyl" denotes a straight-chain or branched-chain saturated hydrocarbon group containing from 1 to 4 carbon atoms such as methyl, ethyl, propyl, isopropyl, tert.butyl and the like. The term "lower alkoxy" denotes a hydrocarbonoxy group containing up to 4 carbon atoms. The term "halogen" denotes chlorine, bromine, fluorine and iodine. The term "residue of an aromatic heterocyclic ring containing from 1 to 4 carbon atoms which may be substituted by one or two lower alkyl groups" includes residues of 5- or 6-membered aromatic heterocyclic rings containing 1-4 nitrogen and/or oxygen and/or sulfur atoms and which may be substituted by one or two lower alkyl groups such as 2-thiazolyl, 4-methyl-2-thiazolyl, 4,5-dimethyl-2-thiazolyl, 5-methyl-1,3,4-thiadiazolyl, 2-pyrazinyl, 2-pyrimidinyl, 1,2,4-triazin-3-yl, 2-pyridyl, 3-pyridyl, 4-pyridyl, 3-methyl-2-pyridyl, 4-methyl-2-pyridyl, 5-methyl-2-pyridyl, 6-methyl-2-pyridyl, 4,6-dimethyl-2-pyridyl, 5-isoxazolyl, 5-methyl-3-isoxazolyl, 3,4-dimethyl-5-isoxazolyl 2,6-dimethyl-4-pyrimidinyl, 6-methyl-2-pyridyl, 1,2,3,4-tetrazol-5-yl and the like.

A preferred group of thienothiazine derivatives of formula I comprises those in which $R_3$ and $R_4$ each represent a hydrogen atom. $R_1$ preferably represents the methyl group. $R_2$ preferably represents the 2-thiazolyl, 5-isoxazolyl or 2-pyridyl group.

An especially preferred thienothiazine derivative of formula I is 4-hydroxy-2-methyl-N-(2-thiazolyl)-2H-thieno[2,3-e]-1,2-thiazine-3-carboxamide 1,1-dioxide.

According to the process provided by the present invention, the thienothiazine derivatives of formula I are manufactured by (a) reacting a compound of the general formula

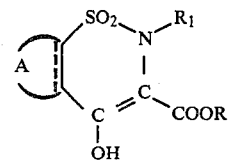   II wherein R represents a lower alkyl group and A and $R_1$ have the significance given earlier,
with an amine of the general formula $$H_2N-R_2 \qquad III$$

wherein $R_2$ has the significance given earlier, or (b) cyclizing a reactive functional derivative of an acid of the general formula

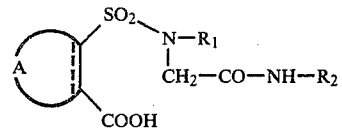   IV wherein A, $R_1$ and $R_2$ have the significance given earlier, or (c) lower alkylating a compound of the general formula

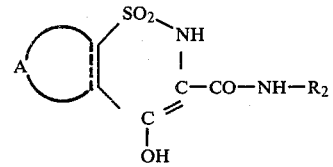   V wherein A and $R_2$ have the significance given earlier.

The reaction of a compound of formula II with an amine of formula III in accordance with embodiment (a) of the present process can be carried out in the presence or absence of an inert solvent. Suitable solvents are alcohols (e.g. ethanol etc.), hydrocarbons (e.g. benzene, toluene, xylene, etc.), halogenated hydrocarbons (e.g. chloroform, chlorobenzene, methylene chloride, carbon tetrachloride, etc.), dimethylformamide or dioxane. The reaction is preferably carried out by heating, the melting point or reflux temperature of the reaction mixture being especially preferred.

According to embodiment (b) of the present process, a reactive functional derivative of an acid of formula IV is cyclized. This cyclization is carried out in the presence of a base and preferably in the presence of a solvent at a temperature between 0° C. and the reflux temperature of the mixture, preferably between room temperature and 60° C. As the base there is especially used a hydride, amide or alcoholate of an alkali metal. Suitable solvents are aprotic and protic solvents such as alcohols (e.g. methanol or ethanol), ethers (e.g. dioxane) and acid amides (e.g. dimethylformamide). The cyclization is expediently carried out by dissolving a reactive functional derivative of an acid of formula IV in a solvent, treating the resulting solution with a base and either allowing the resulting mixture to stand at room temperature for 1 to 4 hours or heating same to a temperature up to 60° C. for 1 to 4 hours. Especially suitable reactive functional derivatives of acids of formula IV are the lower alkyl esters (e.g. the methyl esters).

halide or di(lower alkyl)sulfate, to give a corresponding thienothiazine derivative of formula I. The temperature and pressure at which this lower alkylation is carried out are not critical. For the sake of convenience, the lower alkylation is preferably carried out at room temperature and under atmospheric pressure.

The starting materials of formula II hereinbefore used in embodiment (a) of the process can be prepared according to the following Formula Scheme in which A, R and $R_1$ have the significance given earlier and Hal represents a halogen atom:

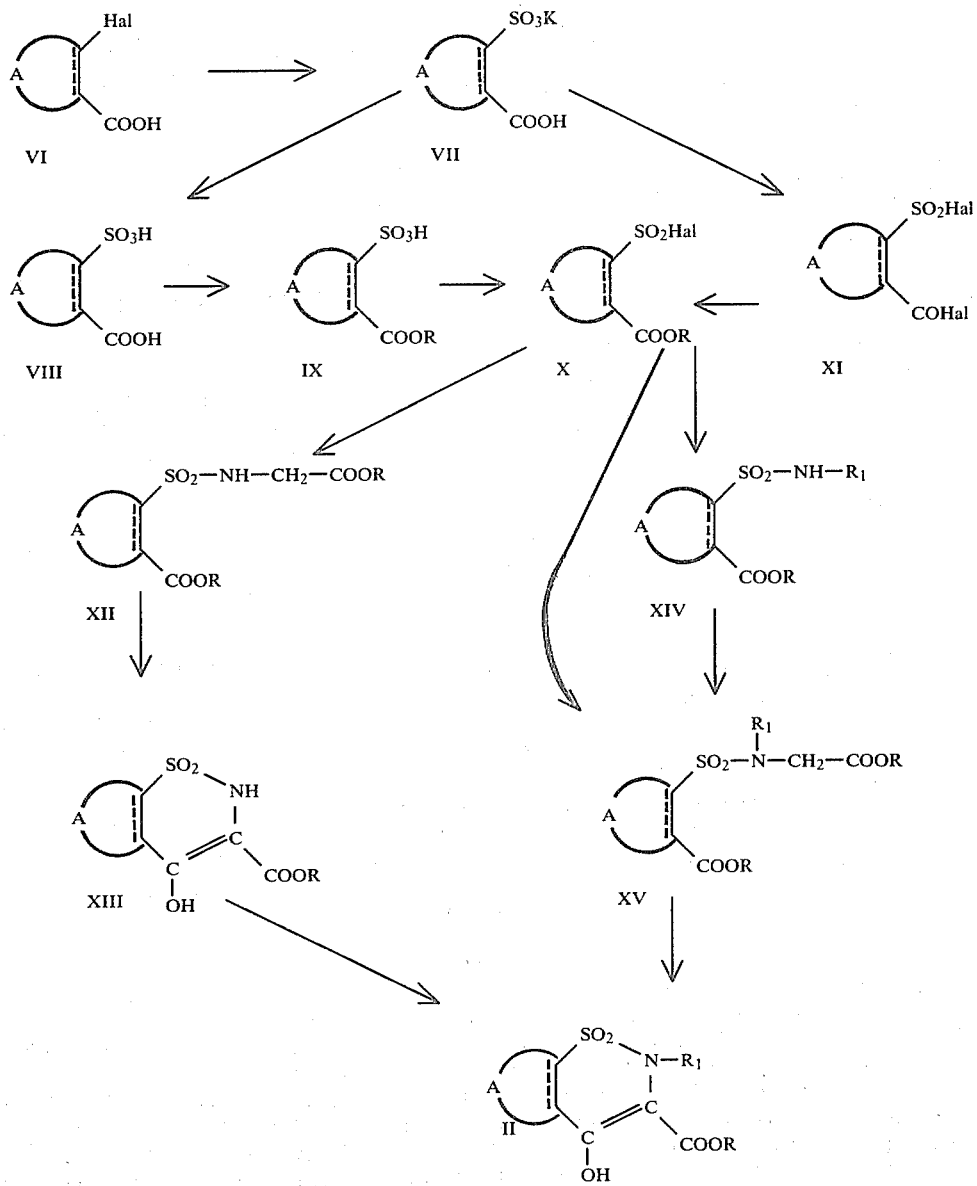

According to embodiment (c) of the present process, a compound of formula V is lower alkylated. This lower alkylation is conveniently carried out by dissolving a compound of formula V in an aprotic solvent (e.g. acetonitrile, dioxane or dimethylformamide), treating the solution with an alkali metal amide or alkali metal hydride to form an alkali metal salt of the compound of formula V and then treating the mixture with an appropriate alkylating agent, especially a lower alkyl Of the compounds of formula VI, 3-chloro-thiophene-2-carboxylic acid and 4-bromo-thiophene-3-carboxylic acid are known, the former having been prepared in a relatively complicated manner. A more facile method for the preparation of 3-chloro-thiophene-2-carboxylic acid consists in converting the known 3-hydroxy-thiophene-2-carboxylic acid methyl ester in an inert solvent boiling above 80° C. (e.g. chloroform or dioxane) with a chlorinating agent (e.g. phosphorus pentachloride) into 3-chloro-thiophene-2-carboxylic acid chloride and hydrolyzing this acid chloride to the corresponding acid. In an analogous manner, there can also be prepared substituted 3-chloro-thiophene-2-carboxylic acids (compounds of formula VI in which Hal represents a chlorine atom and A together with the two carbon atoms to which it is attached forms the group

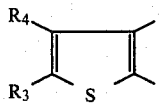

in which $R_3$ and/or $R_4$ represents other than a hydrogen atom). Although for the preparation of a compound of formula VII there can, in principle, also be used a bromo compound (e.g. the known 4-bromo-thiophene-3-carboxylic acid) it is recommended to use the corresponding chloro compound. 4-Chloro-thiophene-3-carboxylic acid, which has not been described in the literature, can be prepared from the known 3-keto-thiophene-4-carboxylic acid methyl ester by converting this ester by means of phosphorus pentachloride with aromatization into 4-chloro-thiophene-3-carboxylic acid chloride and hydrolyzing this acid chloride to the corresponding acid. In an analogous manner there can also be prepared substituted 4-chloro-thiophene-3-carboxylic acids (compounds of formula VI in which Hal represents a chlorine atom and A together with the two carbon atoms to which it is attached forms the group

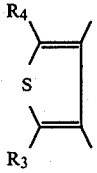

in which $R_3$ and/or $R_4$ represents other than a hydrogen atom).

The conversion of a halothiophene carboxylic acid of formula VI into a potassium salt of a sulfothiophene carboxylic acid of formula VII is carried out according to methods known per se by reaction with sodium hydrogen sulfite in the presence of a copper (I) salt catalyst, especially copper (I) chloride, and reacting the product obtained with potassium chloride. The reaction with sodium hydrogen sulfide should be carried out at a temperature of 143° C. in order to obtain optimum yields.

The conversion of a compound of formula VII into the free acid of formula VIII is carried out in a manner known per se; for example, with a strong ion exchanger.

The esterification of an acid of formula VIII to give an ester of formula IX is carried out autocatalytically (presence of the sulfo group) in an alcohol/chloroform mixture. For the formation of the methyl ester, the acid is dissolved in methanol/chloroform and the mixture obtained is heated to the boiling point of the ternary azeotrope (methanol/chloroform/reaction water).

The conversion of a compound of formula IX into an acid halide of formula X is carried out in a manner known per se using a halogenating agent, preferably a chlorinating agent such as thionyl chloride or phosphorus pentachloride. The chlorination using thionyl chloride can be carried out in the absence of a solvent by heating to reflux. The chlorination with phosphorus pentachloride can be carried out in the presence of an inert solvent (e.g. chloroform, carbon tetrachloride or dioxane) and at a temperature between 50° C. and the reflux temperature of the mixture.

A compound of formula X can, however, also be prepared from a potassium salt of a sulfothiophene carboxylic acid of formula VII via a compound of formula XI. In this procedure, the chosen potassium salt is reacted, for example, with 2 mols of phosphorus pentachloride and in the presence of phosphorus oxychloride as the solvent at a temperature between 30° C. and the boiling point of phosphorus oxychloride. However, in place of phosphorus oxychloride, there can also be used an inert organic solvent (e.g. dioxane, chloroform, carbon tetrachloride, benzene, toluene and the like).

The esterification of a compound of formula XI to give a corresponding ester of formula X is carried out using an appropriate alcohol, especially methanol, at a temperature between room temperature and the reflux temperature of the mixture. As the solvent there can be used the alcohol or an inert solvent (e.g. chloroform, carbon tetrachloride, dioxane or benzene).

The starting materials of formula II can be prepared from the compounds of formula X according to two different routes. The first route proceeds via compounds of formulae XII and XIII and the second route proceeds via compounds of formula XV, optionally via compounds of formula XIV.

According to the first of the above-mentioned routes, a compound of formula X is reacted in a manner known per se with a glycine alkyl ester hydrochloride, preferably glycine ethyl ester hydrochloride. The reaction is preferably carried out in the presence of an inert solvent (e.g. pyridine, chloroform, dioxane, methylene chloride, benzene or carbon tetrachloride) and at room temperature. The compound of formula XII obtained in this manner is cyclized to a compound of formula XIII in which R represents the ethyl group by treatment in ethanol at a temperature between 40° C. and 65° C. with an alkali metal ethylate or alkaline earth metal ethylate, especially sodium ethylate. The alkylation to give a starting material of formula II is carried out in a manner known per se; conveniently in a polar aprotic solvent (e.g. dimethylformamide, dimethylsulfoxide or hexametapol) with an alkylating agent such as an alkyl halide or a dialkyl sulfate at a temperature between 0° C. and room temperature.

According to the second of the aforementioned methods, a compound of formula X is either aminoalkylated to give a compound of formula XIV and this is converted into a compound of formula XV or a compound of formula X is converted directly into a compound of formula XV. In both of these cases, a compound of formula XV obtained is cyclized to a compound of formula II.

The aminoalkylation of a compound of formula X is carried out in a manner known per se by reaction with an alkylamine in the presence of an inert organic solvent (e.g. chloroform, methylene chloride, carbon tetrachloride, benzene or dioxane) and at room temperature.

For the preparation of a compound of formula XV, a thus-obtained compound of formula XIV is reacted in a manner known per se in the presence of a polar aprotic solvent (e.g. dimethylformamide, dimethylsulfoxide or hexametapol) with a compound of the general formula $$X-CH_2-COO-R \qquad XVI$$

wherein R has the significance given earlier and X represents a halogen atom. The reaction is conveniently carried out at a temperature between 0° C. and room temperature.

Alternatively, a compound of formula XV is obtained in a manner known per se by reacting a compound of formula X with a compound of the general formula

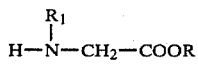   XVII wherein R and $R_1$ have the significance given earlier, or an acid addition salt thereof.

The reaction is conveniently carried out at room temperature. When an acid addition salt of formula XVII is used, the reaction is expediently carried out in pyridine. In place of an acid addition salt there can, however, also be used 2 mols of free amine, in which case the reaction is preferably carried out in dioxane, methylene chloride, benzene or carbon tetrachloride.

The cyclization of a compound of formula XV to give a starting material of formula II is conveniently carried out at a temperature between room temperature and 65° C. using an alkali metal or alkaline earth metal methylene or ethylate, preferably sodium methylate or sodium ethylate in the presence of methanol or ethanol.

p The compounds of formulae XVI and XVII are known or can be prepared in a manner known per se.

The lower alkyl esters of acids of formula IV used as starting materials in embodiment (b) of the present process can be obtained by reacting an amine of formula III hereinbefore with chloroacetyl chloride and reacting the resulting compound of the general formula

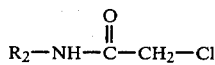   XVIII wherein $R_2$ has the significance given earlier, with a compound of formula XIV hereinbefore. Other reactive functional derivatives of acids of formula IX can be prepared in a manner known per se from the esters obtained.

The starting materials of formula V required for embodiment (c) of the process can be obtained by reacting a compound of formula XIII hereinbefore with an amine of formula III hereinbefore.

The compounds of formulae H, IV, V and XII to XV are novel and it will be appreciated that these compounds and their preparation also form part of the present invention.

The thienothiazine derivatives provided by this invention have an antiinflammatory, analgesic and antirheumatic activity. These valuable pharmacological properties can be determined using standard methods; for example, the known kaolin paw oedema test (on the rat). In this test, an acute local inflammation is produced in the right hind paw of the rat by intradermal injection of 0.1 ml. of a 10% kaolin suspension (bolus alba). The substance to be tested is administered orally and the following parameters are measured:

1. Diameter of the paw in mm (as an expression of the intensity of inflammation);
2. Pressure in g of the paw (to determine the pain threshhold).

0.5 Hour before and 3.5 hours after the kaolin injection, the substance to be tested is administered and 4 hours after the kaolin injection the parameters mentioned earlier are measured. The oedema-inhibiting effect is specified in percentage based on the difference of oedema intensity between untreated animals and animals treated with the substance to be tested, the antinociceptive activity being specified by the percentage increase of the pain threshold.

In the foregoing test, 4-hydroxy-2-methyl-N-(2-thiazolyl)-2H-thieno-[2,3-e]-1,2-thiazine-3-carboxamide 1,1-dioxide [$LD_{50}$ about 900 mg/kg, p.o. mouse)] shows a 27% oedema inhibition and a 4% increase of the pain threshold at a dosage of 3 mg/kg p.o. and shows a 43% oedema inhibition and a 23% increase of the pain threshold at a dosage of 10 mg/kg p.o.

The thienothiazine derivatives provided by this invention possess an activity qualitatively similar to that of phenylbutazone which is known for its therapeutic use and properties.

The thienothiazine derivatives provided by the present invention can be used as medicaments; for example, in the form of pharmaceutical preparations which contain them in association with a compatible pharmaceutical carrier material. This carrier material can be an organic or inorganic inert carrier material suitable for enteral or parenteral administration such as, for example, water, gelatin, gum arabic, lactose, starch, magnesium stearate, talc, vegetable oils, polyalkylene glycols, petroleum jelly, etc. The pharmaceutical preparations can be made up in a solid form (e.g. as tablets, dragees, suppositories or capsules), in a semi-solid form (e.g. as ointments) or in a liquid form (e.g. as solutions, suspensions or emulsions). The pharmaceutical preparations may be sterilized and/or may contain adjuvants such as preservatives, stabilizers, emulsifiers, salts for varying the osmotic pressure or buffers. The pharmaceutical preparations may also contain therapeutically valuable substances other than the thienothiazine derivatives provided by the present invention.

The following Examples illustrate the process provided by the present invention.

EXAMPLE 1

52.1 g. of phosphorus pentachloride are dissolved in 600 ml. of absolute carbon tetrachloride and heated to boiling, whereupon a solution of 15.8 g. of 3-hydroxy-2-methoxycarbonyl-thiophene in 200 ml. of carbon tetrachloride is added dropwise during 3 hours. The mixture is boiled to reflux for 13 hours, the carbon tetrachloride is distilled off and the mixture is evaporated almost to dryness in vacuo. 450 Ml. of water are added dropwise while cooling, whereupon the mixture is heated to boiling and then allowed to cool. The resulting precipitate is filtered off under suction and boiled up with 10 g. of active carbon in a solution of 25 g. of sodium bicarbonate. The active carbon is then filtered off under suction and the cooled solution is acidified with hydrochloric acid. There is obtained 3-chlorothiophene-2-carboxylic acid of melting point 185°–186° C.

In a glass autoclave, 8.6 g. of 3-chlorothiophene-2-carboxylic acid are dissolved in 23 ml. of water containing 2.1 g. of sodium hydroxide, whereupon a solution of 5.6 g. of sodium bisulfite in 16 ml. of water is added and the solution made just alkaline with a 30% sodium hydroxide solution. The mixture is then treated with 0.43 g. of copper (I) chloride and heated at 143° C. for 16 hours. After cooling, the red copper oxide is filtered off under suction. The filtrate is then acidified with 7 ml. of concentrated hydrochloric acid, by which means the unreacted starting material precipitates out. The latter is removed by shaking out with methylene chloride. The acidic solution is treated with 12 g. of potassium chloride while warming and, after cooling to 0° C., the potassium salt of 3-sulfothiophene-2-carboxylic acid separates as colorless crystals.

8.2 G. of the potassium salt of 3-sulfothiophene-2-carboxylic acid are dissolved in 50 ml. of water. This solution is passed through an ion-exchange column which is charged with protons, after which the column is rinsed with water until the solution flowing out has a pH value of 5. The solution is evaporated to dryness in vacuo and the crystalline residue is recrystallized from a small amount of water. There is obtained pure 3-sulfothiophene-2-carboxylic acid.

7.6 G. of 3-sulfothiophene-2-carboxylic acid are dissolved in 140 ml. of absolute methanol and 65 ml. of absolute chloroform and boiled to reflux. The water of reaction is distilled off over a packed column (1 m) as a ternary azeotrope (chloroform, methanol, water). The mixture is evaporated in vacuo. To remove traces of methanol, the residue is treated with 100 ml. of chloroform and the resulting mixture evaporated under atmospheric pressure. The remaining brown oil consists of 3-sulfothiophene-2-carboxylic acid methyl ester and crystallizes immediately after cooling. However, the crystals are hygroscopic and deliquesce in the air.

7.4 G. of crude 3-sulfothiophene-2-carboxylic acid methyl ester are dissolved in 50 ml. of thionyl chloride and boiled to reflux for 16 hours. The mixture is then evaporated to dryness in vacuo and the remaining bright-yellow oil is brought to crystallization with petroleum ether. There is obtained 3-chlorosulfonylthiophene-2-carboxylic acid methyl ester.

20 G. of 3-chlorosulfonylthiophene-2-carboxylic acid methyl ester are dissolved in absolute chloroform, whereupon 21 g. of sarcosine ethyl ester are added dropwise during 10 minutes. In so doing, the mixture warms up to 50° C. After 20 minutes, the mixture is cooled, shaken once each time with water, 0.5 -N hydrochloric acid and a sodium bicarbonate solution, dried and evaporated. The remaining oil is brought to crystallization with ethanol. There is obtained 3-(N-carbethoxymethyl-N-methyl-sulfamoyl)-thiophene-2-carboxylic acid methyl ester of melting point 84°–85° C.

13.2 G. of 3-(N-carbethoxymethyl-N-methyl-sulfamoyl)-thiophene-2-carboxylic acid methyl ester are suspended in 42 ml. of a 1-N methanolic sodium methylate solution in the cold and under a nitrogen stream. After stirring for 15 minutes, a clear solution results. The solution is heated to reflux for 20 minutes, then cooled, neutralized and evaporated in vacuo. The residue is taken up in methylene chloride, shaken once each time with water and a sodium bicarbonate solution, dried and evaporated. The residue is brought to crystallization with methanol. There is obtained 3-carbomethoxy-4-hydroxy-2-methyl-2H-thieno[2,3-e]-1,2-thiazine 1,1-dioxide of melting point 193°–195° C.

1.9 G. of 3-carbomethoxy-4-hydroxy-2-methyl-2H-thieno[2,3-e]-1,2-thiazine 1,1-dioxide are suspended together with 0.9 g. of 2-aminothiazole in 250 ml. of absolute xylene and heated to reflux for 7 hours, by which means 150 ml. of xylene are slowly distilled off. The residual xylene is then evaporated in vacuo. The crystalline residue is recrystallized from ethanol. There is obtained 4-hydroxy-2-methyl-N-(2-thiazolyl)-2H-thieno[2,3-e]-1,2-thiazine-3-carboxamide 1,1-dioxide of melting point 217° C. (decomposition).

EXAMPLE 2

50 G. (0.203 mol) of the monopotassium salt of 3-sulfothiophene-2-carboxylic acid are suspended in 250 ml. of phosphorus oxychloride and while stirring there are added 84 g. (0.406 mol) of phosphorus pentachloride [vigorous hydrogen chloride evolution]. The mixture is then heated on the water bath while stirring for a further 90 minutes and then cooled to room temperature. The inorganic salts are filtered off under suction and the phosphorus oxychloride distilled off in vacuo as well as possible. To remove inorganic salts still present, the oily residue is dissolved in 400 ml. of dry chloroform, filtered and evaporated. The oily residue crystallizes on cooling and consists of 3-chlorosulfonylthiophene-2-carboxylic acid chloride.

48 G. (0.196 mol) of the obtained 3-chlorosulfonylthiophene-2-carboxylic acid chloride are dissolved in 500 ml. of absolute chloroform, 9.6 g. (0.3 mol) of absolute methanol are added and the mixture is heated to reflux for 3 hours [until no more hydrogen chloride evolution]. The mixture is evaporated to dryness in vacuo and the residue allowed to crystallize. There is obtained pure 3-chlorosulfonylthiophene-2-carboxylic acid methyl ester.

43.5 G. (0.18 mol) of the obtained 3-chlorosulfonyl-thiophene-2-carboxylic acid methyl ester are dissolved in 450 ml. of absolute chloroform and dry methylamine is led through the solution at 10° C. until a moistened pH paper shows an alkaline reaction with the solution. The mixture is then allowed to react at room temperature for a further 2 hours, the solution always remaining alkaline. The solution is then shaken out with 500 ml. of water and 500 ml. of a 5% sodium bicarbonate solution [the aqueous phases are back-extracted in each case once with chloroform]. The combined organic phases are dried over sodium sulfate and then evaporated. The crystalline residue is digested with ether for purification. There is obtained 3-methylsulfamoylthiophene-2-carboxylic acid methyl ester of melting point 115°–122° C.

43.5 G. (0.184 mol) of the obtained 3-methylsulfamoyl-thiophene-2-carboxylic acid methyl ester are dissolved in 400 ml. of absolute dimethylformamide are added dropwise at 0° C. during 1 hour to a stirred suspension of 4.5 g. (0.187 mol) of sodium hydride in 50 ml. of absolute dimethylformamide. Then, 40 g. (0.187 mol) of iodoacetic acid ethyl ester dissolved in 50 ml. of absolute dimethylformamide are added dropwise during 2 hours while cooling at 0°–5° C. and the mixture allowed to react for a further 1 hour [until a moistened pH paper shows a pH of 7–8]. The mixture is evaporated in vacuo and the residue taken up with 300 ml. of 0.5-N hydrochloric acid and 300 ml. of methylene chloride. The organic phase is separated, the aqueous phase is back-extracted twice with a small amount of methylene chloride and the combined organic phases are shaken out twice with 100 ml. each time of a 5% sodium bicarbonate solution [the aqueous phases are back-extracted once each time with a small amount of methylene chloride]. The combined organic phases are dried over sodium sulfate and evaporated. The crystalline residue is digested with a small amount of cold ethanol for purification. There is obtained 3-(N-carbethoxymethyl-N-methylsulfamoyl)-thiophene-2-carboxylic acid methyl ester of melting point 83°–85° C.

13.2 G. (0.041 mol) of the obtained 3-(N-carbethoxymethyl-N-methylsulfamoyl)-thiophene-2-carboxylic acid methyl ester are suspended in 42 ml. of a 1-N methanolic sodium methylate solution in the cold and under a nitrogen atmosphere, everything dissolving after stirring for 15 minutes. The solution is heated to reflux for 25 minutes, cooled, neutralized with concentrated hydrochloric acid and evaporated in vacuo. The residue is taken up in methylene chloride, shaken out once each time with water and a 5% sodium bicarbonate solution, dried and evaporated. The crystalline residue is digested with a small amount of methanol for purification. There is obtained 4-hydroxy-3-methoxycarbonyl-2-methyl-2H-thieno[2,3-e]-1,2-thiazine 1,1-dioxide of melting point 193°–195° C., which can be converted by reaction with 2-aminothiazole in a manner analogous to that described in the last part of Example 1 into the 4-hydroxy-2-methyl-N-(2-thiazolyl)-2H-thieno[2,3-e]-1,2-thiazine-3-carboxamide 1,1-dioxide of melting point 217° C. (decomposition).

EXAMPLE 3

50 G. (0.203 mol) of the monopotassium salt of 3-sulfothiophene-2-carboxylic acid are suspended in 250 ml. of phosphorus oxychloride and while stirring there are added 85 g. (0.406 mol) of phosphorus pentachloride [vigorous hydrogen chloride evolution]. The mixture is then heated on the water bath while stirring for a further 90 minutes and cooled to room temperature. The inorganic salts are filtered off under suction and the phosphorus oxychloride distilled off in vacuo as well as possible. To remove inorganic salts still present, the oily residue is dissolved in 400 ml. of dry chloroform, filtered and evaporated. The oily residue crystallizes on cooling and consists of 3-chlorosulfonylthiophene-2-carboxylic acid chloride.

48 G. (0.196 mol) of the obtained 3-chlorosulfonylthiophene-2-carboxylic acid chloride are dissolved in 500 ml. of absolute chloroform, 9.6 g. (0.3 mol) of absolute methanol are added and the solution is heated to reflux for 3 hours [until no more hydrogen chloride evolution]. The mixture is evaporated to dryness in vacuo and the residue allowed to crystallize out. There is obtained pure 3-chlorsulfonylthiophene-2-carboxylic acid methyl ester. 2.41 G. (0.010 mol) of the obtained 3-chlorosulfonylthiophene-2-carboxylic acid methyl ester are dispersed together with 1.53 g. of sarcosine ethyl ester hydrochloride in 10 ml. of absolute pyridine and stirred at room temperature. After 2 hours, the mixture is poured on to 50 ml. of ice-cold 2-N hydrochloric acid and extracted five times with 20 ml. of methylene chloride each time. The combined organic phases are dried over sodium sulfate, filtered and evaporated. The crystalline residue is digested with a small amount of ice-cold ethanol.

13.2 G. (0.041 mol) of the obtained 3-(N-carbethoxymethyl-N-methylsulfamoyl)-thiophene-2-carboxylic acid methyl ester are suspended in 42 ml. of a 1-N methanolic sodium methylate solution in the cold and under a nitrogen atmosphere, everything dissolving after stirring for 15 minutes. The solution is heated to reflux for 25 minutes, cooled, neutralized with concentrated hydrochloric acid and evaporated in vacuo. The residue is taken up in methylene chloride, shaken out once each time with water and a 5% sodium bicarbonate solution, dried and evaporated. The crystalline residue is digested with a small amount of methanol for purification. There is obtained 4-hydroxy-3-methoxycarbonyl-2-methyl-2H-thieno[2,3-e]-1,2-thiazine 1,1-dioxide of melting point 193°–195° C., which can be converted by reaction with 2-aminothiazole in a manner analogous to that described in the last part of Example 1 into the 4-hydroxy-2-methyl-N-(2-thiazolyl)-2H-thieno[2,3-e]-1,2-thiazine-3-carboxamide 1,1-dioxide of melting point 217° C. (decomposition).

EXAMPLE 4

12.03 G. (0.05 mol) of 3-chlorosulfonylthiophene-2-carboxylic acid methyl ester and 7 g. (0.05 mol) of glycine ethyl ester hydrochloride are suspended in 50 ml. of absolute pyridine, everything dissolving within 30 minutes. The solution is stirred at room temperature for a further 5 hours and the pyridine subsequently distilled off. The residue is taken up in 50 ml. of 2-N hydrochloric acid and 50 ml. of methylene chloride, the organic phase is separated and the aqueous layer back-extracted four times with a small amount of methylene chloride. The combined organic phases are washed with water and dried over sodium sulfate with addition of active carbon. After filtration, the filtrate is evaporated. The oily residue consists of 3-(N-carbethoxymethyl-sulfamoyl)-thiophene-2-carboxylic acid methyl ester.

A solution of 9.22 g. (0.03 mol) of the obtained 3-(N-carbethoxymethylsulfamoyl)-thiophene-2-carboxylic acid methyl ester in 10 ml. of ethanol is added at 40° C. to a solution of 1.38 g. (0.06 mol) of sodium in 20 ml. of absolute ethanol and the mixture heated to 60°–65° C. The mixture is stirred for a further 2 hours at this temperature, then poured on to 100 ml. of ice-cold 2-N hydrochloric acid and shaken out several times with a small amount of methylene chloride. The combined organic extracts are shaken out twice with 20 ml. each time of a 5% sodium acetate solution and then four times with 25 ml. each time of a 10% sodium carbonate solution. By drying and evaporation of the organic phase, there can be recovered 2.5 g. of starting material. The combined carbonate extracts are acidified with hydrochloric acid and shaken out with methylene chloride. After drying over sodium sulfate, the solvent is distilled off and the crystalline residue digested with a small amount of ether. There is obtained 3-ethanocarbonylmethyl-4-hydroxy-2H-thieno[2,3-e]-1,2-thiazine 1,1-dioxide of melting point 148°–150° C.

1.93 G. (7 mmol) of 3-ethoxycarbonylmethyl-4-hydroxy-2H-thieno[2,3-e]-1,2-thiazine 1,1-dioxide are dissolved in 4 ml. of absolute dimethylformamide and added dropwise during 30 minutes at 0° C. to a stirred suspension of 0.185 g. (7.7 mmol) of sodium hydride in 2 ml. of absolute dimethylformamide. The mixture is stirred for a further 1 hour at room temperature. There are then added firstly 0.53 ml. (1.2 g.; 8.45 mmol) of methyl iodide and, after 30 minutes, a further 0.25 ml. (0.565 g; 4 mmol) of methyl iodide and the mixture is allowed to react for 1 hour. After distillation of the solvent, the residue is taken up in 30 ml. of 0.5-N hydrochloric acid and 30 ml. of methylene chloride, the organic phase is separated and the aqueous layer is back-extracted twice with a small amount of methylene chloride. The combined organic extracts are dried over sodium sulfate and evaporated. The crystalline residue is digested with a small amount of cold ethanol. There is obtained 3-ethoxycarbonylmethyl-4-hydroxy-2-methyl-2H-thieno[2,3-e]-1,2-thiazine 1,1-dioxide of melting point 161°–163° C. (crystal transformation at 151°–152° C).

In a manner analogous to that described in the last paragraph of Example 1, the 3-ethoxycarbonylmethyl-4-hydroxy-2-methyl-2H-thieno[2,3-e]-1,2-thiazine 1,1- dioxide can be converted with 2-aminothiazole to give 4-hydroxy-2-methyl-N-(2-thiazolyl)-2H-thieno[2,3-e]-1,2-thiazine-3-carboxamide 1,1-dioxide (decomposition point 217° C.).

EXAMPLE 5

25 G. of 3-keto-thiophene-4-carboxylic acid methyl ester dissolved in a small amount of absolute carbon tetrachloride are added dropwise during 2 hours to a boiling solution of 100 g. of phosphorus pentachloride in 250 ml. of absolute carbon tetrachloride. The mixture is then boiled to reflux for a further 15 hours until termination of the hydrogen chloride evolution and evaporated in vacuo, the bulk of the phosphorus chlorides being expelled. The residue is stirred with ice-water for 1 hour, whereupon the organic phase is separated and the aqueous phase shaken out once more with methylene chloride. The combined organic phases are dried over sodium sulfate and evaporated. The remaining brown oil consists of 4-chlorothiophene-3-carboxylic acid chloride. This oil is heated with a 2-N aqueous sodium hydroxide solution at 50° C. until a homogeneous brown solution results. The latter is shaken out once with methylene chloride and acidified with concentrated hydrochloric acid. The precipitated crystals are filtered off under suction and consist of crude 4-chlorothiophene-3-carboxylic acid. For purification, the crystals are dissolved in a sodium bicarbonate solution and re-precipitated with concentrated hydrochloric acid; melting point 164° C. (recrystallization from water).

In a glass autoclave, 8.6 g. of 4-chlorothiophene-3-carboxylic acid are dissolved in 23 ml. of water containing 2.1 g. of sodium hydroxide, whereupon a solution of 5.6 g. of sodium bisulfite in 16 ml. of water is added and the solution made just alkaline with a 30% sodium hydroxide solution. The solution is treated with 0.43 g. of copper (I) chloride and heated at 143° C. for 16 hours. After cooling, the red copper oxide is filtered off under suction. The filtrate is acidified with 7 ml. of concentrated hydrochloric acid and the unreacted starting material precipitates out, the latter being removed by shaking out with ether. The acidic solution is treated with 12 g. of potassium chloride while warming and, after cooling to 0° C., the potassium salt of 4-sulfothiophene-3-carboxylic acid separates as colorless crystals. The crystals are dissolved in 50 ml. of water and the solution passed through an ion-exchange column which is charged with protons, after which the column is rinsed with water until the solution flowing out has a pH value of 5. The eluate is evaporated to dryness in vacuo. There is obtained 4-sulfothiophene-3-carboxylic acid as a crystalline residue of melting point 154° C. (recrystallization from water).

7.6 G. of 4-sulfothiophene-3-carboxylic acid are dissolved in 140 ml. of absolute methanol and 65 ml. of absolute chloroform and boiled to reflux. The water of reaction is distilled off over a packed column (1 m) as a ternary azeotrope (chloroform, methanol, water). The mixture is evaporated in vacuo. To remove traces of methanol, the residue is treated with 100 ml. of chloroform, whereupon the solution is evaporated at atmospheric pressure. The remaining brown oil crystallized immediately after cooling and consists of 4-sulfothiophene-3-carboxylic acid methyl ester [hygroscopic crystals which deliquesce in the air].

7.4 G. of crude 4-sulfothiophene-3-carboxylic acid methyl ester are dissolved in 50 ml. of thionyl chloride and boiled at reflux for 16 hours. The mixture is then evaporated to dryness in vacuo and the remaining bright-yellow oil is brought to crystallization with petroleum ether. There is obtained 4-chlorosulfonylthiophene-3-carboxylic acid methyl ester of melting point 71° C. (recrystallization from petroleum ether).

50 G. of 4-chlorosulfonylthiophene-3-carboxylic acid methyl ester are dissolved in 500 ml. of absolute chloroform. Dry methylamine is led through the solution while cooling until a moistened indicator paper shows a persistent basic reaction. The precipitated methylammonium chloride is removed by shaking out with water. The organic phase is dried and evaporated. The remaining brightyellow oil crystallizes immediately. There is obtained 4-(N-methyl-sulfamoyl)thiophene-carboxylic acid methyl ester of melting point 142° C.

46 G. of 4-(N-methyl-sulfamoyl)-thiophene-3-carboxylic acid methyl ester are dissolved in 450 ml. of dimethylformamide. The solution is cooled to 0° C. and treated with 7 g. (20% excess) of sodium hydride, a vigorous hydrogen evolution resulting. The solution is slowly heated to room temperature and treated successively with 32.6 g. of dry potassium iodide and 21.3 g. of chloroacetic acid methyl ester. In so doing, the temperature rises to 45° C. and a white precipitate separates. The dimethylformamide is subsequently evaporated, whereupon the remaining yellow oil is partitioned between 0.5-N hydrochloric acid and methylene chloride. The organic phase is shaken out with sodium bicarbonate and water, dried and evaporated. The remaining yellow oil crystallizes immediately. There is obtained 4-(N-methoxycarbonylmethyl-N-methyl-sulfamoyl)-thiophene-3-carboxylic acid methyl ester of melting point 124° C. (recrystallization from ethanol).

41.6 G. of 4-(N-methoxycarbonylmethyl-N-methyl-sulfamoyl)-thiophene-3-carboxylic acid methyl ester are taken up in 140 ml. of a 1-N sodium methylate solution and dissolved while boiling at reflux. The solution rapidly turns deep-red via yellow; after 20 minutes the solution becomes turbid by precipitate formation. The mixture is cooled, acidified and evaporated in vacuo. The residue is taken up in methylene chloride and water. The organic phase is shaken with a sodium bicarbonate solution and water and finally extracted with a cooled 0.5-N sodium hydroxide solution. By acidification of the aqueous sodium hydroxide solution, the 4-hydroxy-3-methoxycarbonyl-2-methyl-2H-thieno[3,4-c]1,2-thiazine 1,1-dioxide is obtained in the form of colorless crystals of melting point 190° C. (recrystallization from methanol).

0.9 G. of 4-hydroxy-3-methoxycarbonyl-2-methyl-2H-thieno[3,4-e]-1,2-thiazine 1,1-dioxide are suspended together with 0.4 g. of 2-aminothiazole in 100 ml. of absolute xylene and heated to reflux for 4 hours, 70 ml. of xylene being slowly distilled off. A crystalline precipitate separates from the cooled solution and is filtered off under suction. There is obtained 4-hydroxy-2-methyl-N-(2-thiazolyl)-2H-thieno[3,4-e]-1,2-thiazine-3-carboxamide 1,1-dioxide of melting point 243°–245° C. (decomposition).

EXAMPLE 6

94.6 G. (0.384 mol) of the monopotassium salt of 4-sulfothiophene-3-carboxylic acid are suspended in 390 ml. of phosphorus oxychloride and while stirring there are added 160.8 g. (0.768 mol) of phosphorus pentachloride [vigorous hydrogen chloride evolution]. The mixture is then heated on the water bath while stirring for 3 hours and cooled to room temperature. The inorganic salts are filtered off and the phosphorus oxychloride distilled off in vacuo as well as possible. To remove inorganic salts still present, the residue is dissolved in 400 ml. of dry chloroform, filtered and evaporated. The residue crystallizes on cooling and consists of 4-chlorosulfonylthiophene-3-carboxylic acid chloride.

44.1 G. (0.18 mol) of the obtained 4-chlorosulfonylthiophene-3-carboxylic acid chloride are dissolved in 450 ml. of absolute chloroform, 9.6 g. (0.3 mol) of absolute methanol are added and the solution is heated to reflux for 9 hours [until termination of the hydrogen chloride evolution]. The mixture is then evaporated to dryness in vacuo, the residue crystallizing out. There is obtained 4-chlorosulfonylthiophene-3-carboxylic acid methyl ester, which can be converted into the 4-hydroxy-2-methyl-N-(2-thiazolyl)-2H-thieno[3,4-e]-1,2-thiazine-3-carboxamide 1,1-dioxide in a manner analogous to that described in the last four paragraphs of Example 5.

EXAMPLE 7

By reacting 3-amino-5-methyl-isoxazole with 3-carbomethoxy-4-hydroxy-2-methyl-thieno[2,3-e]-1,2-thiazine 1,2-dioxide for 7 hours in a manner analogous to that described in Example 1, there is obtained 4-hydroxy-2-methyl-N-(5-methyl-3-isoxazolyl)-2H-thieno[2,3-e]-1,2-thiazine-3-carboxamide 1,1-dioxide of decomposition point 239°-243° C.

EXAMPLE 8

By reacting with 3-carbomethoxy-4-hydroxy-2-methyl-thieno[2,3-e]-1,2-thiazine 1,1-dioxide for 7 hours in a manner analogous to that described in Example 1, there is obtained 4-hydroxy-2-methyl-2H-thieno[2,3-e]-1,2-thiazine-3-carboxanilide 1,1-dioxide of decomposition point 248°-251° C. (recrystallization from xylene).

EXAMPLE 9

By reacting 2-pyridylamine with 3-carbomethoxy-4-hydroxy-2-methylthieno[2,3-e]-1,2-thiazine 1,1-dioxide for 7 hours in a manner analogous to that described in Example 1, there is obtained 4-hydroxy-2-methyl-N-(2-pyridyl)-2H-thieno[2,3-e]-1,2-thiazine-3-carboxamide 1,1-dioxide of decomposition point 209°-213° C. (recrystallization from xylene).

EXAMPLE 10

By reacting 3-pyridylamine with 3-carbomethoxy-4-hydroxy-2-methylthieno[2,3-e]-1,2-thiazine 1,1-dioxide for 7 hours in a manner analogous to that described in Example 1, there is obtained 4-hydroxy-2-methyl-N-(3-pyridyl)2H-thieno[2,3-e]-1,2-thiazine-3-carboxamide 1,1-dioxide of decomposition point 241°-244° C. (recrystallization from pyridine).

EXAMPLE 11

By reacting 4-pyridylamine with 3-carbomethoxy-4-hydroxy-2-methylthieno[2,3-e]-1,2-thiazine 1,1-dioxide for 7 hours in a manner analogous to that described in Example 1, there is obtained 4-hydroxy-2-methyl-N-(4-pyridyl)-2H-thieno[2,3-e]-1,2-thiazine-3-carboxamide 1,1-dioxide of decomposition point 263°-267° C. (recrystallization from dimethylformamide).

EXAMPLE 12

By reacting 4-hydroxyaniline with 3-carbomethoxy-4-hydroxy-2-methylthieno[2,3-e]-1,2-thiazine 1,1-dioxide for 7 hours in a manner analogous to that described in Example 1, there is obtained 4,4'-dihydroxy-2-methyl-2H-thieno[2,3-e]-1,2-thiazine-3-carboxanilide 1,1-dioxide of decomposition point 287°-290° C. (recrystallization from dioxane).

EXAMPLE 13

By reacting 3-methylaniline with 3-carbomethoxy-4-hydroxy-2-methylthieno[2,3-e]-1,2-thiazine 1,1-dioxide for 7 hours in a manner analogous to that described in Example 1, there is obtained 4-hydroxy-2-methyl-2H-thieno[2,3-e]-1,2-thiazine-3-carboxy-m-toluidide 1,1-dioxide of decomposition point 197°-199° C. (recrystallization from benzene; crystal transformation at 185°-188° C.).

EXAMPLE 14

By reacting 3-chloroaniline with 3-carbomethoxy-4-hydroxy-2-methylthieno[2,3-e]-1,2-thiazine 1,1-dioxide for 7 hours in a manner analogous to that described in Example 1, there is obtained 3'-chloro-4-hydroxy-2-methyl-2H-thieno[2,3-e]-1,2-thiazine-3-carboxanilide 1,1-dioxide of decomposition point 241°-243° C. (recrystallization from xylene).

EXAMPLE 15

By reacting aminopyrazine with 3-carbomethoxy-2-hydroxy-2-methylthieno[2,3-e]-1,2-thiazine 1,1-dioxide for 7 hours in a manner analogous to that described in Example 1, there is obtained 4-hydroxy-2-methyl-N-pyrazinyl-2H-thieno[2,3-e]-1,2-thiazine-3-carboxamide 1,1-dioxide of decomposition point 245°-248° C. (recrystallization from xylene).

EXAMPLE 16

By reacting 5-amino-3,4-dimethyl-isoxazole with 3-carbomethoxy-4-hydroxy-2-methyl-thieno[2,3-e]-1,2-thiazine 1,1-dioxide for 14 hours in a manner analogous to that described in Example 1, there is obtained N-(3,4-dimethyl-5-isoxazolyl)-4-hydroxy-2-methyl-2H-thieno[2,3-e]-1,2-thiazine-3-carboxamide 1,1-dioxide of decomposition point 206°-208° C. (recrystallisation from benzene).

EXAMPLE 17

By reacting 4-amino-2,6-dimethyl-pyrimidine with 3-carbomethoxy-4-hydroxy-2-methyl-thieno[2,3-e]-1,2-thiazine 1,1-dioxide for 7 hours in a manner analogous to that described in Example 1, there is obtained N-(2,6-dimethyl-4-pyrimidinyl)-4-hydroxy-2-methyl-2H-thieno[2,3-e]-1,2-thiazine-3-carboxamide 1,1-dioxide of decomposition point 270°-271° C. (recrystallisation from xylene).

EXAMPLE 18

By reacting 2-amino-6-methyl-pyridine with 3-carbomethoxy-4-hydroxy-2-methyl-thieno[2,3-e]-1,2-thiazine 1,1-dioxide for 7 hours in a manner analogous to that described in Example 1, there is obtained 4-hydroxy-2-methyl-N-(6-methyl-2-pyridyl)-2H-thieno[2,3-e]-1,2-thiazine-3-carboxamide 1,1-dioxide of decomposition point 216°-218° C. (recrystallisation from benzene).

EXAMPLE 19

By reacting 5-amino-1,2,3,4-tetrazole with 3-carbomethoxy-4-hydroxy-2-methyl-thieno[2,3-e]-1,2-thiazine 1,1-dioxide for 14 hours in a manner analogous to that described in Example 1, there is obtained 4- hydroxy-2-methyl-N-(1,2,3,4-tetrazol-5-yl)-2H-thieno[2,3-e]-1,2-thiazine-3-carboxamide 1,1-dioxide of decomposition point 244° C. (recrystallisation from ethanol).

EXAMPLE 20

By reacting 2-amino-pyrimidine with 3-carbomethoxy-4-hydroxy-2-methyl-thieno[2,3-e]-1,2-thiazine 1,1-dioxide for 18 hours in a manner analogous to that described in Example 1, there is obtained 4-hydroxy-2-methyl-N-(2-pyrimidinyl)-2H-thieno[2,3-e]-1,2-thiazine-3-carboxamide 1,1-dioxide of decomposition point 221°-223° C. (recrystallisation from ethanol).

EXAMPLE 21

0.82 g (0.003 mol) of 3-ethoxycarbonyl-4-hydroxy-2H-thieno[2,3-e]-1,2-thiazine 1,1-dioxide are suspended together with 0.4 g (0.004 mol) of 2-aminothiazole in 100 ml of absolute xylene and the mixture is heated to boiling. 50 ml of solvent are slowly distilled off azeotropically with the resulting ethanol during 7 hours. After 2 hours, 4-hydroxy-N-(2-thiazolyl)-2H-thieno[2,3-e]-1,2-thiazine-3-carboxamide 1,1-dioxide begins to crystallise out. After cooling, the crystals are filtered off, washed with petroleum ether and, if desired, recrystallised from xylene or dioxane; melting point 289°-290° C. (decomposition).

0.329 g (1 mmol) of 4-hydroxy-N-(2-thiazolyl)-2H-thieno[2,3-e]-1,2-thiazine-3-carboxamide 1,1-dioxide are dissolved in 2 ml of absolute dimethylformamide and added at 0° C. to a stirred suspension of 0.026 g (1.1 mmol) of sodium hydride in 1 ml of absolute dimethylformamide. The mixture is stirred at room temperature for a further 1 hour. 0.1 ml (0.226 g; 1.6 mmol) of methyl iodide are then added to the sodium salt solution and allowed to react for a further 1 hour. After distillation of the solvent, the residue is taken up in 200 ml of methylene chloride and 10 ml of 0.5-N hydrochloric acid. The organic phase is separated and shaken out with a total of 50 ml of a 0.5% sodium bicarbonate solution. The aqueous layer, which now contains the desired product, is back-extracted several times with methylene chloride and acidified with hydrochloric acid. The acidic aqueous phase is extracted with methylene chloride and the combined organic extracts dried over sodium sulphate and evaporated. The crystalline residue is digested with a sall amount of cold ethanol for purification. There is obtained 4-hydroxy-2-methyl-N-(2-thiazolyl)-2H-thieno[2,3-e]-1,2-thiazine-3-carboxamide 1,1-dioxide of melting point 217° C. (decomposition).

EXAMPLE 22

40 g (0.4 mol) of 2-aminothiazole are dissolved in 400 ml of absolute dioxane and treated with 100 g of freshly ignited potassium carbonate. 95 ml of chloroacetyl chloride are then added portionwise, the temperature rising to 70° C. The mixture is stirred for 90 minutes and subsequently poured on to an ice-cold solution of 150 g of potassium carbonate in 4000 ml of water, 2-chloroacetylaminothiazole precipitating out. The mixture is stirred for a further 1 hour and filtered under vacuum. The residue is washed well with water and recrystallised from ethanol; melting point 176°-177° C.

b 0.5 g (2.12 mmol) of methylsulphamoyl-thiophene-2-carboxylic acid methyl ester are dissolved in 8 ml of absolute dimethylformamide and added at 0° C. to a stirred suspension of 0.06 g of sodium hydride in 2 ml of absolute dimethylformamide. The mixture is stirred at room temperature for a further 1 hour. 0.38 g (2.15 mmol) of the previously obtained 2-chloroacetylaminothiazole and 0.36 g (2.17 mmol) of potassium iodide are added to the sodium salt solution and the mixture is stirred for a further 2 hours. After distillation of the solvent, the residue is taken up in 20 ml of 0.5-N hydrochloric acid and 50 ml of methylene chloride and the aqueous phase shaken out several times with methylene chloride. The combined organic phases are washed with water, dried over sodium sulphate, filtered and evaporated. There is obtained 3-[N-(2-thiazolylcarbamoyl-methyl)-N-methyl]-sulphamoyl-thiophene-2-carboxylic acid methyl ester.

0.1 g (0.27 mmol) of 3-[N-(2thiazolyl-carbamoyl-methyl)-N-methyl]-sulphamoyl-thiophene-2-carboxylic acid methyl ester are dissolved in 5 ml of absolute dimethylformamide and treated with 0.01 g of sodium hydride. After stirring for 2 hours, the desired 4-hydroxy-2-methyl-N-(2-thiazolyl)-2H-thieno[2,3-e]-1,2-thiazine-3-carboxamide 1,1-dioxide can be detected by thin-layer chromatography.

The following Examples illustrate typical pharmaceutical preparation containing a thienothiazine derivative provided by the present invention:

EXAMPLE A

In the normal manner, suppositories of the following composition are manufactured:

| | |
|---|---|
| 4-Hydroxy-2-methyl-N-(2-thiazolyl)-2H-thieno[2,3-e]-1,2-thiazine-3-carboxamide 1,1-dioxide | 0.025 g |
| Hydrogenated cocoanut oil | 1.230 g |
| Carnauba wax | 0.045 g |

EXAMPLE B

In the normal manner, tablets of the following composition are manufactured:

| | Per tablet |
|---|---|
| 4-Hydroxy-2-methyl-N-(2-thiazolyl)-2H-thieno[2,3-e]-1,2-thiazine-3-carboxamide 1,1-dioxide | 25.00 mg |
| Lactose | 64.50 mg |
| Maize starch | 10.00 mg |
| Magnesium stearate | 0.50 mg |
| Total weight | 100.00 mg |

EXAMPLE C

In the normal manner, capsules of the following composition are manufactured:

| | Per capsule |
|---|---|
| 4-Hydroxy-2-methyl-N-(2-thiazolyl)-2H-thieno[2,3-e]-1,2-thiazine-3-carboxamide 1,1-dioxide | 50 mg |
| Lactose | 125 mg |
| Maize starch | 30 mg |
| Talc | 5 mg |
| Total weight | 210 mg |

We claim:

1. A reactive functional derivative of an acid of the formula

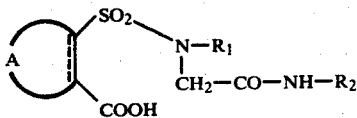

wherein A together with the two carbon atoms to which it is attached forms the group

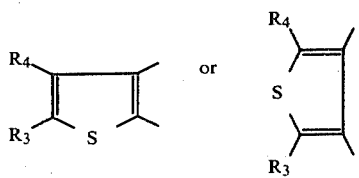

and the broken line represents the double bond present in group (a); $R_1$ represents a lower alkyl group; $R_2$ is selected from the group consisting of 2-thiazolyl, 4-methyl-2-thiazolyl, 4,5-dimethyl-2-thiazolyl, 5-methyl-1,3,4-thiadiazolyl, 2-pyrazinyl, 2-pyrimidinyl, 1,2,4-triazin-3-yl, 2-pyridyl, 3-pyridyl, 4-pyridyl, 3-methyl-2-pyridyl, 4-methyl-2-pyridyl, 5-methyl-2-pyridyl, 6-methyl-2-pyridyl, 4,6-dimethyl-2-pyridyl, 5-isoxazolyl, 5-methyl-3-isoxazolyl, 3,4-dimethyl-5-isoxazolyl, 2,6-dimethyl-4-pyrimidinyl and 6-methyl-2-pyridyl group or a phenyl group which may be substituted by halogen, hydroxy, lower alkyl, trifluoromethyl or lower alkoxy; and $R_3$ and $R_4$ each represent a hydrogen atom or a lower alkyl group.

* * * * *